United States Patent
Harding et al.

(10) Patent No.: US 7,874,730 B2
(45) Date of Patent: Jan. 25, 2011

(54) SYSTEMS AND METHODS FOR REDUCING A DEGRADATION EFFECT ON A SIGNAL

(75) Inventors: Geoffrey Harding, Hamburg (DE); Johannes Paul Delfs, Hamburg (DE)

(73) Assignee: Morpho Detection Inc., Newark, CA (US)

( * ) Notice: Subject to any disclaimer, the term of this patent is extended or adjusted under 35 U.S.C. 154(b) by 2 days.

(21) Appl. No.: 12/005,843

(22) Filed: Dec. 28, 2007

(65) Prior Publication Data

US 2009/0166551 A1 Jul. 2, 2009

(51) Int. Cl.
*G01D 18/00* (2006.01)
(52) U.S. Cl. ...................................... 378/207
(58) Field of Classification Search .............. 378/6, 378/7, 70, 86–90, 18, 19, 45–50, 205, 207
See application file for complete search history.

(56) References Cited

U.S. PATENT DOCUMENTS

| | | | |
|---|---|---|---|
| 4,963,746 A | | 10/1990 | Morgan et al. |
| 4,985,906 A | * | 1/1991 | Arnold .................. 378/18 |
| 5,450,883 A | * | 9/1995 | Payne et al. ............ 141/59 |
| 5,682,412 A | | 10/1997 | Skillicorn et al. |
| 6,807,248 B2 | | 10/2004 | Mihara et al. |
| 6,816,564 B2 | | 11/2004 | Charles, Jr. et al. |
| 6,917,396 B2 | | 7/2005 | Hiraishi et al. |
| 6,975,752 B2 | | 12/2005 | Dixon et al. |
| 7,283,613 B2 | | 10/2007 | Harding |
| 2007/0158573 A1 | | 7/2007 | Deych |
| 2007/0263770 A1 | | 11/2007 | Harding |
| 2009/0080600 A1 | * | 3/2009 | Keller et al. ............ 378/18 |

FOREIGN PATENT DOCUMENTS

DE 19603000 A1 7/1997

OTHER PUBLICATIONS

Phys. Med. Biol., vol. 21, No. 5, Robert E. Alvarez and Albert Macovski, Energy-Selective Reconstructions in X-Ray Computerized Tomograpy, Feb. 1976, Stanford, CA, pp. 733-744,.
J. Phys. Chem. Ref. Data, vol. 4, No. 3, 1975, J. H. Hubbell, Wm. J. Veigele and E. A. Briggs, and R.T. Brown and D.T. Cromer and R. J. Howerton, Atomic Form Factors, Incoherent Scattering Functions, and Photon Scattering Cross Sections. 1975. pp. 471-538.
European Search Report regarding Application No. 08172085.6-1240 / 2075572, Nov. 17, 2009, 6 pages, Europe.
Geoffrey Harding et al., "Liquids Identification with X-Ray Diffraction," Sep. 24, 2007, 12 pages, vol. No. 6707, ISSN: 0277-786X, Proceedings of the Spie—The International Society for Optical Engineering, US.
Geoffrey Harding, "Effective Density and Atomic Number Determined from Diffraction Profiles," Aug. 30, 2006, 10 pages, vol. No. 6319, ISSN: 0277-786X, Proceedings of the Spie—The International Society for Optical Engineering, US.

* cited by examiner

*Primary Examiner*—Irakli Kiknadze
(74) *Attorney, Agent, or Firm*—Armstrong Teasdale, LLP

(57) ABSTRACT

Systems and methods for reducing a degradation effect on a signal are described. One of the methods includes pre-processing data based on a scan of a reference object and a scan of a substance. The reference object includes a material having an atomic number ranging from and including forty to sixty.

19 Claims, 5 Drawing Sheets

US 7,874,730 B2

SYSTEMS AND METHODS FOR REDUCING A DEGRADATION EFFECT ON A SIGNAL

FIELD OF THE INVENTION

The field of the invention relates generally to accounting for attenuation of radiation by a substance and, more particularly, to systems and methods for reducing a degradation effect created by the attenuation on a signal.

BACKGROUND OF THE INVENTION

The events of Sep. 11, 2001 instigated an urgency for more effective and stringent screening of airport baggage. The urgency for security expanded from an inspection of carry-on bags for knives and guns to a complete inspection of checked bags for a range of hazards with particular emphasis upon concealed explosives. X-ray imaging is a widespread technology currently employed for screening. In an X-ray imaging system, an X-ray source transmits X-rays towards a detector and the detector detects the X-rays to identify a set of materials.

Identification systems based on X-ray diffraction (XRD) techniques provide an improved discrimination of the materials compared to that provided by the X-ray imaging system. The XRD identification systems also include the detector and measure d-spacings between lattice planes of micro-crystals in materials. A "d-spacing" is a perpendicular distance between adjacent lattice planes in any of the materials.

However, the XRD identification systems suffer from degradation effects on a signal detected by the detector. The effects are created by self-attenuation of diffracted X-rays by an item, such as a bag, under investigation. If these degradation effects are not reduced, a threat material within the item may be difficult to identify and the difficulty in identification leads to a false alarm rate in identifying the threat material.

BRIEF DESCRIPTION OF THE INVENTION

A brief description of embodiments of systems and methods for reducing a degradation effect on a signal follows.

In one aspect, a method for reducing a degradation effect on a signal is described. The method includes pre-processing data based on a scan of a reference object and a scan of a substance. The reference object includes a material having an atomic number ranging from and including forty to sixty.

In another aspect, a system for reducing a degradation effect on a signal is described. The system includes an X-ray source configured to generate X-rays and a reference object configured to output scattered radiation upon receiving the X-rays. The reference object includes a material having an atomic number ranging from and including forty to sixty. The system further includes a detector configured to output an electrical signal by detecting the scattered radiation.

In yet another aspect, a method for reducing a degradation effect on a signal is described. The method includes generating pre-processed data as a function of an intensity of scattered radiation detected by a detector element upon scanning a substance, an intensity of scattered radiation detected by the detector element upon scanning a reference object, a Photoelectric pathlength of the substance, a Compton pathlength of the substance, a Photoelectric pathlength of the reference object, and a Compton pathlength of the reference object.

In yet another aspect, a system for reducing a degradation effect on a signal is described. The system includes an X-ray source configured to generate X-rays, a reference object configured to output a first set of transmission radiation and scattered radiation upon receiving the X-rays, and a substance configured to output a second set of transmission radiation and scattered radiation upon receiving the X-rays. The system further includes a dual-energy transmission detector configured to detect the transmission radiation within the first and second sets, and a scatter detector including a detector element and configured to detect the scattered radiation within the first and second sets. The system includes a processor coupled to the dual-energy transmission detector and the scatter detector. The processor is configured to generate pre-processed data as a function an intensity of the scattered radiation within the first set, an intensity of the scattered radiation within the second set, a Photoelectric pathlength of the substance, a Compton pathlength of the substance, a Photoelectric pathlength of the reference object, and a Compton pathlength of the reference object.

BRIEF DESCRIPTION OF THE DRAWINGS

FIG. 1 is an isometric view of an embodiment of a system for reducing a degradation effect on a signal.

FIG. 2 is an embodiment of a graph showing a molecular interference function of silver nitrate solution, which is suitable for use within the system of FIG. 1.

FIG. 3 is a front-view of an embodiment of a dual-energy transmission detector, which is suitable for use within the system of FIG. 1.

FIG. 4 is block diagram of an embodiment of a system for reducing a degradation effect on a signal.

FIG. 5 is a block diagram of an embodiment of a system for generating an X-ray image.

FIG. 6 is a flowchart of an embodiment of a method for reducing a degradation effect on a signal.

DETAILED DESCRIPTION OF THE INVENTION

While described in terms of detecting contraband including, without limitation, weapons, explosives, and/or narcotics, within baggage, the embodiments described herein can be used for any suitable diffraction imaging application.

Figure 1:
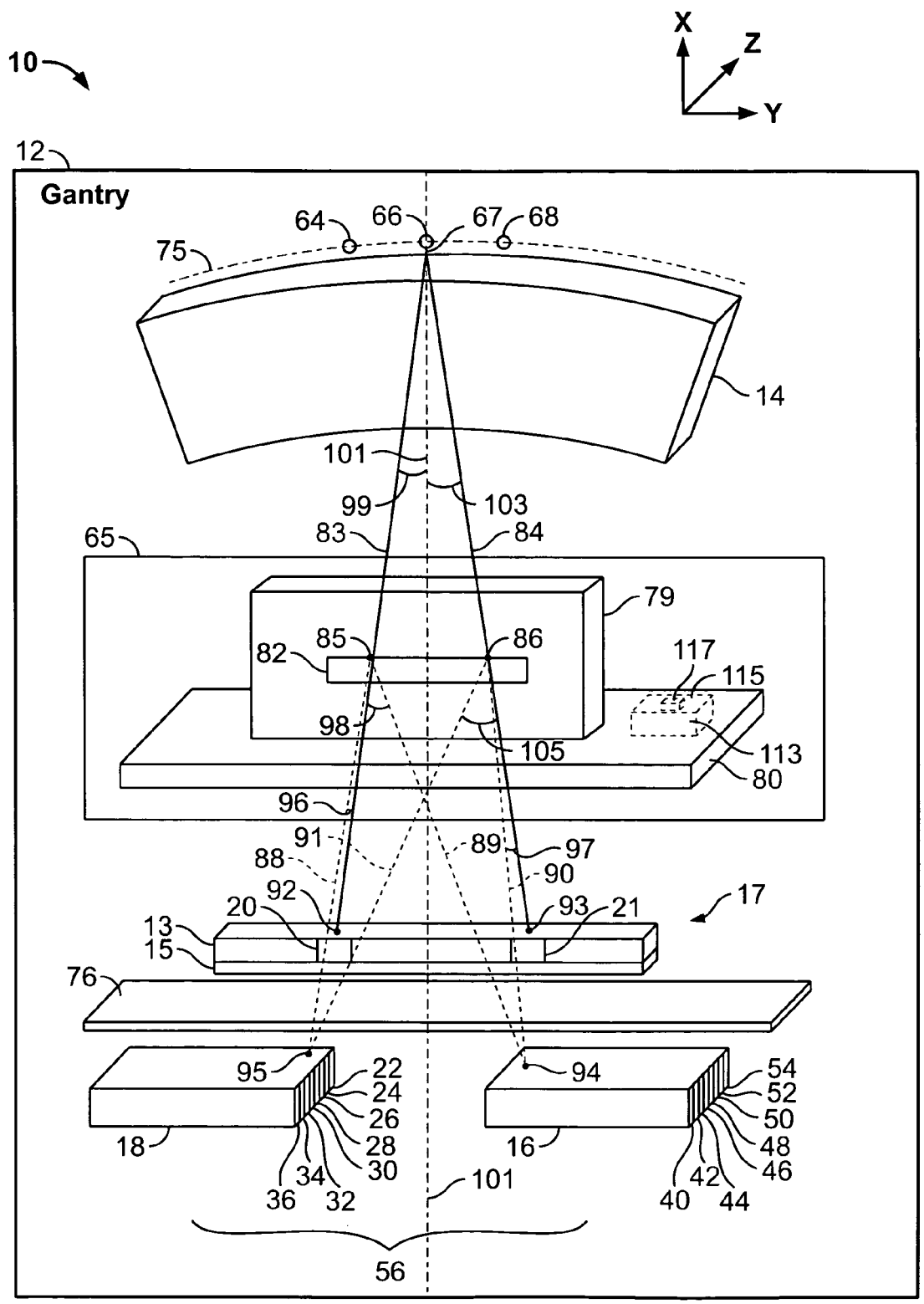
FIGS. 1-6 show embodiments of systems and methods for reducing a degradation effect on a signal.
Figure 2:
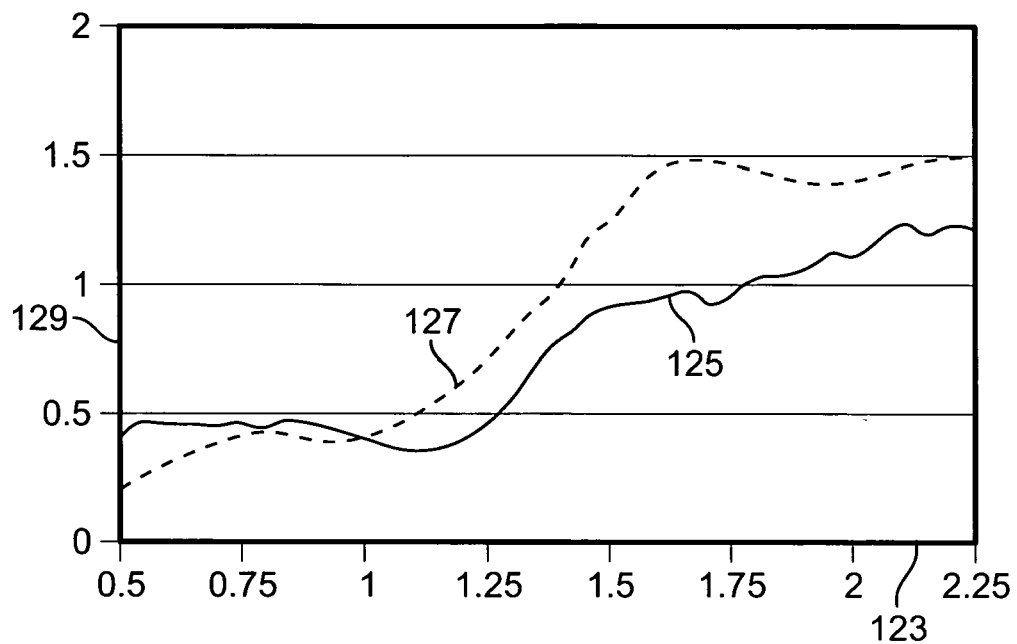

FIG. 1 is an isometric view of an embodiment of a system 10 for reducing a degradation effect on a signal and FIG. 2 is an exemplary graph showing characteristics of a reference object used within the system of FIG. 1. System 10 includes a gantry 12. Gantry 12 includes a primary collimator 14, which is a multi-focus primary collimator, a scatter detector 16, a transmission detector 17, a scatter detector 18, and a secondary collimator 76. Each scatter detector 16 and 18 is a segmented semiconductor detector.

Transmission detector 17 includes a layer 13 and a layer 15. Layer 13 is a low-energy resolving layer that detects X-rays of low energy, such as ranging from and including 30 kiloelectron volts (keV) to 60 keV. Layer 15 is a high-energy resolving layer that detects X-rays of high energy, such as ranging from and including 60 keV to 150 keV, that is higher than the low-energy. Transmission detector 17 includes a plurality of detector elements, such as detector elements 20 and 21 within layer 13.

Scatter detector 18 includes a plurality of detector cells or detector elements 22, 24, 26, 28, 30, 32, 34, and 36 for detecting coherent scatter. Scatter detector 16 includes a plurality of detector cells or detector elements 40, 42, 44, 46, 48, 50, 52, and 54 for detecting coherent scatter. Each scatter detector 16 and 18 includes any suitable number of detector elements, such as, ranging from and including 5 to 1200 detector elements. For example, scatter detector 18 includes 5 detector elements in a z-direction parallel to a z-axis, and one detector element in a y-direction parallel to a y-axis. As another example, scatter detector 18 includes 20 detector elements in the z-direction, and 20 detector elements in the y-direction. As yet another example, scatter detector 18 includes 40 detector elements in the z-direction, and 30 detector elements in the y-direction. An x-axis, the y-axis, and the z-axis are located within an xyz co-ordinate system having an origin. The x-axis is perpendicular to the y-axis and the z-axis, the y-axis is perpendicular to the z-axis, and the x-axis is parallel to an x-direction. A number of detector elements within scatter detector 16 may be equal to a number of detector elements within scatter detector 18.

Scatter detector 16 is separate from scatter detector 18. For example, scatter detector 16 has a housing that is separate from a housing of scatter detector 18. As another example scatter detectors 16 and 18 are separated from each other by a gap. As yet another example, a shortest distance 56 between a center of scatter detector 16 and a center of scatter detector 18 ranges from and including 40 millimeters (mm) to 200 mm. As another example, shortest distance 56 between a center of scatter detector 16 and a center of scatter detector 18 is 45 mm. As yet another example, shortest distance 56 between a center of scatter detector 16 and a center of scatter detector 18 is 125 mm. As still another example, shortest distance 56 between a center of scatter detector 16 and a center of scatter detector 18 is 195 mm. Each scatter detector 16, scatter detector 18, and transmission detector 17 is located in the same yz plane. The yz plane is formed by the y-axis and the z-axis. Each scatter detector 16 and scatter detector 18 is separated from transmission detector 17 by a shortest distance ranging from and including 30 mm to 60 mm in the z-direction. As an example, each scatter detector 16 and scatter detector 18 is separated from transmission detector 17 by a shortest distance of 35 mm in the z-direction. As another example, each scatter detector 16 and scatter detector 18 is separated from transmission detector 17 by a shortest distance of 50 mm in the z-direction. As yet another example, each scatter detector 16 and scatter detector 18 is separated from transmission detector 17 by a shortest distance of 60 mm in the Z-direction.

Gantry 12 further includes a plurality of X-ray sources 64, 66, and 68. X-ray sources 64, 66, and 68, and transmission detector 17 form an inverse single-pass multi-focus imaging system. X-ray sources 64, 66, and 68 have an inverse fan-beam geometry that includes a symmetric location of the X-ray sources 64, 66, and 68 relative to the z-axis. X-ray sources 64, 66, and 68, are located parallel to and coincident with an arc 75. It is noted that in an alternative embodiment, system 10 includes a higher number, such as 10 or 20, or alternatively a lower number, such as 4 or 6, X-ray sources than that shown in FIG. 1. A center of transmission detector 17 is located at a center of a circle having arc 75. Examples of each X-ray source 64, 66, and 68 include a polychromatic X-ray source. Each X-ray source 64, 66, and 68 is an X-ray source that includes a cathode and an anode. Alternatively, each X-ray source 64, 66, and 68 is an X-ray source that includes a cathode and all X-ray sources 64, 66, and 68 share a common anode.

A container 79 is placed on a support 80 between a set of X-ray sources 64, 66, and 68, and a set of scatter detectors 16 and 18. Container 79 and support 80 are located within an opening 65 of gantry 12. Examples of container 79 include a bag, a box, and an air cargo container. Container 79 includes a substance 82. Examples of substance 82 include a crystalline organic explosive, an amorphous substance having a crystallinity of less than twenty five percent, a quasi-amorphous substance having a crystallinity at least equal to twenty-five percent and less than fifty percent, a partially crystalline substance having a crystallinity at least equal to fifty percent and less than one-hundred percent, and a crystalline substance having a crystallinity of one-hundred percent. Examples of the amorphous, quasi-amorphous, and partially crystalline substances include a gel explosive, a slurry explosive, an explosive including ammonium nitrate, and a special nuclear material. Examples of the special nuclear material include plutonium and uranium. Examples of support 80 include a table and a conveyor belt. An example of each scatter detector 16 and 18 includes a segmented detector fabricated from Germanium.

System 10 further includes a reference object 113 placed within a reference object housing 115. Reference object housing 115 is hermetically sealed and has a hermetically sealed cap 117 to confine reference object 113. Reference object housing 115 moves on support 80 within an object space, such as opening 65, to move reference object 113 within the object space. The object space is a space, such as opening 65, in which substance 82 is moved. Hermetically sealed cap 117 is opened, by a user, to pour reference object 113 into reference object housing 115 and is closed by the user after pouring reference object 113 into reference object housing 115. Reference object housing 115 protects reference object 113 from ambient light. Reference object housing 115 may be made of plastic and may be opaque to light. For example, reference object housing 115 is opaque to light by having a dark color, such as black or navy blue. The dark color protects reference object 113 from receiving ambient light.

Reference object 113 is separate from substance 82. Reference object 113 does not extend parallel to a length of arc 75 extending from the left-most X-ray source (not shown) in system 10 to the right-most X-ray source (not shown) in system 10 and reference object 113 is shorter than the length. Reference object 113 includes a material having an atomic number from and including 40 to 60. An example of the material includes silver. Another example of reference object 113 includes a silver nitrate ($AgNO_3$) solution stored within reference object housing 115. Yet another example of reference object 113 includes a dilute solution of silver nitrate solution, which is silver nitrate mixed with water. Yet another example of reference object 113 includes a stabilized solution including silver nitrate, water, and nitric acid ($HNO_3$) having a weight percent ranging from and including 0.001 to 0.005.

A graph 125, shown in FIG. 2, represents a molecular interference function $s_{AgNO_3}(x)$ of a dilute silver nitrate solution, including 75 grams (g) of silver nitrate and 100 g of water, versus a momentum transfer x, which is described below. A graph 127 shows a molecular interference function of a conventional reference object versus the momentum transfer x. The molecular interference function $s_{AgNO_3}(x)$ and the molecular interference function of the conventional reference object are plotted on an ordinate 129 and the momentum transfer x is plotted on abscissa 123. As shown in graph 127, a ratio of a largest value of the conventional reference object to a smallest value of the molecular interference function of the conventional reference object is greater than three. On the other hand, as shown in graph 125, a ratio of a largest value of the molecular interference function $s_{AgNO_3}(x)$ to a smallest value of the molecular interference function $s_{AgNO_3}(x)$ is reduced to three or less than three and this ratio reduces photon noise in a diffraction profile that may be pre-processed by the methods for reducing a degradation effect on a signal mentioned below.

Referring back to FIG. 1, X-ray source 66 emits an X-ray beam 67 in an energy range, which is dependent on a voltage applied by a power source to X-ray source 66. Primary collimator 14 generates two primary beams 83 and 84, such as pencil beams, after collimating X-ray beam 67 from X-ray source 66. Primary beams 83 and 84 are examples of transmission radiation. In an alternative embodiment, primary collimator 14 collimates X-ray beam 67 received from X-ray source 66 to generate a plurality, such as three or four, primary beams. A number of primary beams generated by primary collimator 14 is equal to or alternatively greater than a number of scatter detectors on one side of transmission detector 17 and on one side of the y-axis. Primary beams 83 and 84 pass through a plurality of points 85 and 86 on substance 82 within container 79 arranged on support 80 to generate scattered radiation 88, 89, 90, and 91. For example, primary beam 83 passes through point 85 to generate scattered radiation 88 and 89. As another example, primary beam 84 passes through point 86 to generate scattered radiation 90 and 91.

Secondary collimator 76 is located between support 80 and scatter detectors 16 and 18. Secondary collimator 76 includes a number of collimator elements, such as sheets, slits, or laminations, to ensure that scattered radiation arriving at scatter detectors 16 and 18 have constant scatter angles with respect to primary beams 83 and 84 and that a position of scatter detectors 16 and 18 permits a depth in container 79 at which the scattered radiation originated to be determined. For example, the collimator elements of secondary collimator 76 are arranged parallel to a direction of scattered radiation 88 and of scattered radiation 90 to absorb scattered radiation that is not parallel to the direction of scattered radiation 88 and of scattered radiation 90.

The number of collimator elements in secondary collimator 76 is equal to or alternatively greater than a number of detector elements of scatter detectors 16 and/or 18. The collimator elements are arranged such that scattered radiation between neighboring collimator elements is incident on one of the detector elements. The collimator elements of scatter detectors 16 and 18 are made of a radiation-absorbing material, such as steel, copper, silver, or tungsten.

Transmission detector 17 is positioned underneath support and configured to measure an intensity of primary beam 83 at a point 92 on transmission detector 17 and an intensity of primary beam 84 at a point 93 on transmission detector 17. Transmission detector 17 provides electrical output signals corresponding to the low and high energies of X-rays, such as primary beams 83 and 84, incident on transmission detector 17.

Scatter detectors 16 and 18 that measure photon energies of scattered radiation are positioned underneath support 80 and configured to measure photon energies of scattered radiation received by scatter detectors 16 and 18. Each scatter detector 16 and 18 measures the X-ray photons within scattered radiation received by scatter detectors 16 and 18 in an energy-sensitive manner by outputting a plurality of electrical output signals linearly dependent on a plurality of energies of the X-ray photons detected from within the scattered radiation. Scatter detector 16 measures scattered radiation 90 received at a point 94 on scatter detector 16 and scatter detector 18 measures scattered radiation 88 received at a point 95 on scatter detector 18. An example of a shortest distance between points 85 and 95 includes a distance ranging from and including 900 mm to 1100 mm. Another example of a shortest distance between points 85 and 95 includes a distance of 925 mm. Yet another example of a shortest distance between points 85 and 95 includes a distance of 1000 mm. Another example of a shortest distance between points 85 and 95 includes a distance of 1095 mm. An example of a distance between points 95 and 92 includes a distance ranging from and including 25 mm to 80 mm. Yet another example of a distance between points 95 and 92 includes a distance of 30 mm. Another example of a distance between points 95 and 92 includes a distance of 50 mm. Yet another example of a distance between points 95 and 92 includes a distance of 75 mm.

Scatter detectors 16 and 18 detect scattered radiation to generate a plurality of electrical output signals. Scatter detector 16 detects scattered radiation 90 generated upon intersection of primary beam 84 with point 86. Moreover, scatter detector 16 detects at least a portion of scattered radiation 89 generated upon intersection of primary beam 83 with point 85. Scatter detector 18 detects scattered radiation 88 generated upon intersection of primary beam 83 with point 85. Moreover, scatter detector 18 detects at least a portion of scattered radiation 91 generated upon intersection of primary beam 84 with point 86. A scatter angle 96 formed between primary beam 83 and scattered radiation 88 is equal to a scatter angle 97 formed between primary beam 84 and scattered radiation 90. An example of each scatter angle 96 and 97 includes an angle ranging from and including 0.025 radians to 0.045 radians. As another example, each scatter angle 96 and 97 includes an angle of 0.03 radians. As yet another example, each scatter angle 96 and 97 includes an angle of 0.04 radians. As still another example, each scatter angle 96 and 97 includes an angle of 0.045 radians. An example of a scatter angle 98 formed between primary beam 83 and scattered radiation 89 ranges from and including 0.05 radians to 0.09 radians. An example of scatter angle 98 includes 0.05 radians. Another example of scatter angle 98 includes 0.07 radians. Yet another example of scatter angle 98 includes 0.09 radians. Moreover, an example of a scatter angle 105 formed between primary beam 84 and scattered radiation 91 ranges from and including 0.05 radians to 0.09 radians. An example of scatter angle 105 includes 0.05 radians. Another example of scatter angle 105 includes 0.07 radians. Yet another example of scatter angle 105 includes 0.09 radians.

Scatter angle 98 is at least two times greater than scatter angles 96 and/or 97 and scatter angle 105 is at least two times greater than scatter angles 96 and/or 97. An angle 99 formed by primary beam 83 with respect to a center 101 between scatter detectors 16 and 18 is equal to an angle 103 formed by primary beam 84 with respect to center 101.

During a time at which reference object 113 is moved within the object space to scan reference object 113, substance 82 is not scanned by system 10. For example, reference object 113 is periodically scanned by using system 10 once or twice a month by system 10. Reference object 113 is placed by a user within system 10 instead of substance 82 and moved on support 80 within the object space.

In an alternative embodiment, system 10 includes additional scatter detectors other than scatter detectors 16 and 18. The additional scatter detectors are placed on a side of transmission detector 17 that includes scatter detectors 16 and 18. Moreover, the additional scatter detectors are the same as scatter detectors 16 and 18. For example, any one of the additional scatter detectors have the same number of detector elements as that of scatter detectors 16 and/or 18. In yet another alternative embodiment, system 10 does not include scatter detector 16. In still another alternative embodiment, a single-focus primary collimator is used instead of primary collimator 14 and one of primary beams 83 and 84 is generated by the single-focus primary collimator. In another alternative embodiment, reference object 113 is moved on a support, such as a table, by a user in at least one of the x, y, and z directions within the object space. In yet another alternative embodiment, layer 13 is a high-energy resolving layer that detects X-rays of the high energy and layer 15 is the low-energy resolving layer that detects X-rays of the low energy. In another alternative embodiment, transmission detector 17 is another multi-energy transmission detector, such as a triple-energy transmission detector. In yet another alternative embodiment, system 10 includes any number, such as one or three, scatter detectors. For example, system 10 does not include scatter detector 16. In another alternative embodiment, reference object 113 is not moved within system 10 to scan reference object 113. For example, reference object 113 is stationary during a scan performed using system 10.

Figure 3:
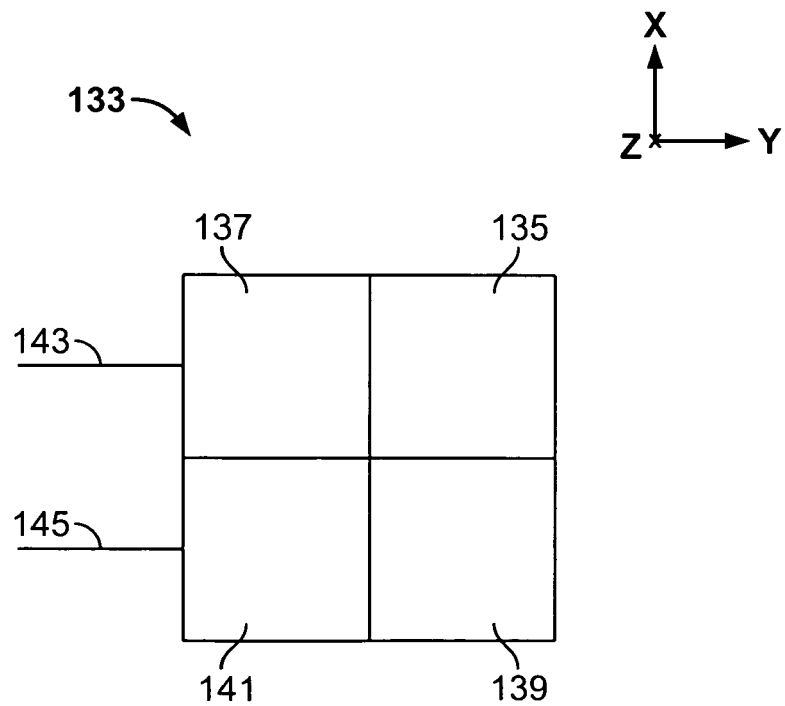

FIG. 3 shows a front-view of an embodiment of a transmission detector 133, which is an example of transmission detector 17. Transmission detector 133 includes a scintillator layer 135, a photodiode 137, a scintillator layer 139, and a photodiode 141. A detector element including scintillator layer 135 and photodiode 137 is an example of detector element 20 or detector element 21 of layer 13 (shown in FIG. 1). A detector element including scintillator layer 139 and photodiode 141 is an example of a detector element of layer 15 (shown in FIG. 1).

Scintillator layers 135 and 139 receive X-rays and converts the X-rays into visible light. For example, scintillator layer 135 receives X-rays, such as primary beams 83 and 84 having the low-energy upon scanning substance 82, and converts the X-rays into visible light. As another example, scintillator layer 139 receives X-rays of the high energy upon scanning substance 82 and converts the X-rays into visible light. Photodiode layer 137 receives visible light from scintillator layer 135 and converts the visible light into a set 143 of electrical output signals that are representative of attenuation by substance 82 and that are representative of the low energy. Similarly, photodiode layer 141 receives visible light from scintillator layer 139 and converts the visible light into a set 145 of electrical output signals representative of attenuation by substance 82 and that are representative of the high energy.

Figure 4:
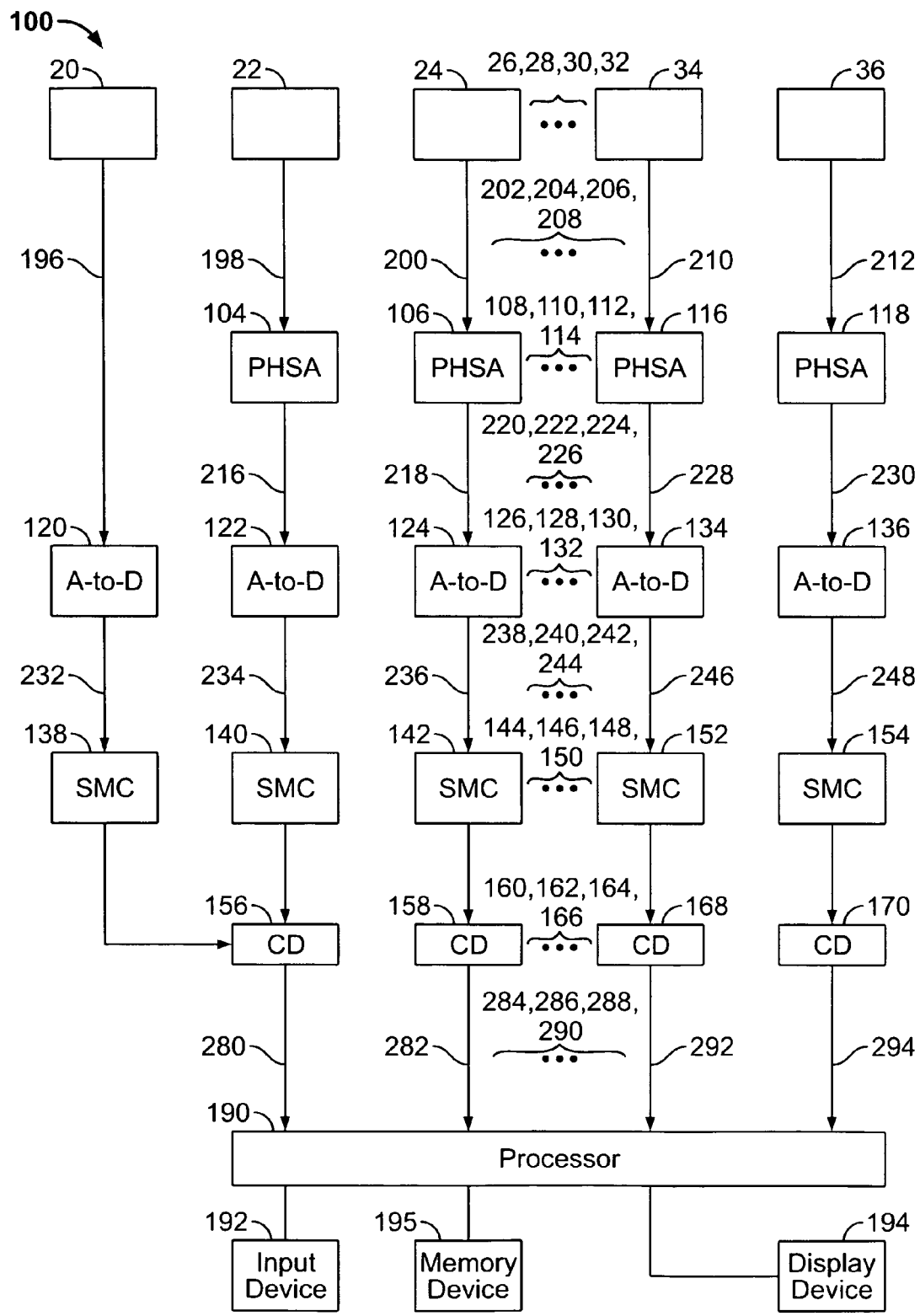

FIG. 4 is block diagram of an embodiment of a system 100 for reducing a degradation effect on a signal. System 100 includes detector element 20 of transmission detector 17, scatter detector elements 22, 24, 26, 28, 30, 32, 34, and 36, a plurality of pulse-height shaper amplifiers (PHSA) 104, 106, 108, 110, 112, 114, 116, and 118, a plurality of analog-to-digital (A-to-D) converters 120, 122, 124, 126, 128, 130, 132, 134, and 136, a plurality of spectrum memory circuits (SMCs) 138, 140, 142, 144, 146, 148, 150, 152, and 154 allowing pulse height spectra to be acquired, a plurality of correction devices (CDs) 156, 158, 160, 162, 164, 166, 168, and 170, a processor 190, an input device 192, a display device 194, and a memory device 195. As used herein, the term processor is not limited to just those integrated circuits referred to in the art as a processor, but broadly refers to a computer, a microcontroller, a microcomputer, a programmable logic controller, an application specific integrated circuit, and any other programmable circuit. The computer may include a device, such as, a floppy disk drive or CD-ROM drive, for reading data including the methods for reducing a degradation effect on a signal from a computer-readable medium, such as a floppy disk, a compact disc-read only memory (CD-ROM), a magneto-optical disk (MOD), or a digital versatile disc (DVD). In an alternative embodiment, processor 190 executes instructions stored in firmware. Examples of display device 194 include a liquid crystal display (LCD) and a cathode ray tube (CRT). Examples of input device 192 include a mouse and a keyboard. Examples of memory device 195 include a random access memory (RAM) and a read-only memory (ROM). An example of each correction device 156, 158, 160, 162, 164, 166, 168, and 170 include a divider circuit. Each spectrum memory circuit 138, 140, 142, 144, 146, 148, 150, 152, and 154 includes an adder and a memory device, such as a RAM or a ROM.

Detector element 20 is coupled to analog-to-digital converter 120, and detector elements 22, 24, 26, 28, 30, 32, 34, and 36 are coupled to pulse-height shaper amplifiers 104, 106, 108, 110, 112, 114, 116, and 118, respectively. Detector element 20 generates an electrical output signal 196 by detecting primary beam 83 and detector elements 22, 24, 26, 28, 30, 32, 34, and 36 generate a plurality of electrical output signals 198, 200, 202, 204, 206, 208, 210, and 212 by detecting scattered radiation. For example, detector element 22 generates electrical output signal 198 for each scattered X-ray photon incident on detector element 22. Each pulse-height shaper amplifier amplifies an electrical output signal received from a corresponding detector element. For example, pulse-height shaper amplifier 104 amplifies electrical output signal 198 and pulse-height shaper amplifier 106 amplifies electrical output signal 200. Pulse-height shaper amplifiers 104, 106, 108, 110, 112, 114, 116, and 118 have a gain factor determined by processor 190.

An amplitude of an electrical output signal output from a detector element is proportional to an energy of an X-ray quantum that is detected by the detector element to generate the electrical output signal. For example, an amplitude of electrical output signal 196 is proportional to an energy of an X-ray quantum in primary beam 83 detected by detector element 20. As another example, an amplitude of electrical output signal 198 is proportional to an energy of an X-ray quantum within scattered radiation that is detected by detector element 22.

A pulse-height shaper amplifier generates an amplified output signal by amplifying an electrical output signal generated from a detector element. For example, pulse-height shaper amplifier 104 generates an amplified output signal 216 by amplifying electrical output signal 198 and pulse-height shaper amplifier 106 generates an amplified output signal 218 by amplifying electrical output signal 200. Similarly, a plurality of amplified output signals 220, 222, 224, 226, 228, and 230 are generated. An analog-to-digital converter converts an output signal from an analog form to a digital form to generate a digital output signal. For example, analog-to-digital converter 120 converts electrical output signal 196 from an analog form to a digital format to generate a digital output signal 232, and analog-to-digital converter 122 converts amplified output signal 216 from an analog form to a digital format to generate a digital output signal 234. Similarly, a plurality of digital output signals 236, 238, 240, 242, 244, 246, and 248 are generated by analog-to-digital converters 124, 126, 128, 130, 132, 134, and 136, respectively. A digital value of a digital output signal generated by an analog-to-digital converter represents an amplitude of energy of a pulse of an amplified output signal. For example, a digital value of digital output signal 234 output by analog-to-digital converter 122 is a value of an amplitude of a pulse of amplified output signal 216. Each pulse is generated by an X-ray quantum, such as an X-ray photon.

An adder of a spectrum memory circuit adds a number of pulses in a digital output signal. For example, when analog-to-digital converter 122 converts a pulse of amplified output signal 216 into digital output signal 234 to determine an amplitude of the pulse of amplified output signal 216, an adder within spectrum memory circuit 140 increments, by one, a value within a memory device of spectrum memory circuit 140. Accordingly, at an end of an X-ray examination of substance 82, a memory device within a spectrum memory circuit stores a number of X-ray quanta detected by a detector element. For example, a memory device within spectrum memory circuit 142 stores a number of X-ray photons detected by detector element 24 and each of the X-ray photons has an amplitude of energy or alternatively an amplitude of intensity that is determined by analog-to-digital converter 124.

A correction device receives a number of X-ray quanta that have a range of energies and are stored within a memory device of one of spectrum memory circuits 140, 142, 144, 146, 148, 150, 152, and 154, and divides the number of X-ray quanta by a number of X-ray quanta having the range of energies received from a memory device of spectrum memory circuit 138. For example, correction device 156 receives a number of X-ray photons having a range of energies from a memory device of spectrum memory circuit 140, and divides the number by a number of X-ray photons having the range received from a memory device of spectrum memory circuit 138. Each correction device outputs a correction output signal that represents a range of energies within X-ray quanta received by a detector element. For example, correction device 156 outputs a correction output signal 280 representing an energy spectrum or alternatively an intensity spectrum within X-ray quanta detected by detector element 22. As another example, correction device 158 outputs correction output signal 282 representing an energy spectrum within X-ray quanta detector element 24. Similarly, a plurality of correction output signals 284, 286, 288, 290, 292, and 294 are generated by correction devices 160, 162, 164, 166, 168, and 170, respectively.

It is noted that a number of pulse-height shaper amplifiers 104, 106, 108, 110, 112, 114, 116, and 118 changes with a number of scatter detector elements 22, 24, 26, 28, 30, 32, 34, and 36. For example, five pulse-height shaper amplifiers are used for amplifying signals received from five corresponding scatter detector elements. As another example, four pulse-height shaper amplifiers are used for amplifying signals received from four corresponding scatter detector elements. Similarly, a number of analog-to-digital converters 120, 122, 124, 126, 128, 130, 132, 134, and 136 changes with a number of detector elements 20, 22, 24, 26, 28, 30, 32, 34, and 36 and a number of spectrum memory circuits 138, 140, 142, 144, 146, 148, 150, 152, and 154 changes with the number of detector elements 20, 22, 24, 26, 28, 30, 32, 34, and 36. In an alternative embodiment, a detector element of layer 15 generates an electrical output signal upon detecting primary beam 83 and the signal is provided to analog-to-digital converter 120 instead of electrical output signal 196.

Processor 190 receives correction output signals 280, 282, 284, 286, 288, 290, 292, and 294 to generate the momentum transfer x, measured in inverse nanometers ($nm^{-1}$), from an energy spectrum r(E) of energy E of X-ray quanta within scattered radiation detected by scatter detector 18 (shown in FIG. 1). Processor 190 generates the momentum transfer x by applying $$x=(E/hc)\sin(\theta/2) \qquad \text{Eq. (1)}$$

where c is a speed of light, h is Planck's constant, θ represents a constant scatter angle of X-ray quanta of scattered radiation detected by scatter detector 18. An example of θ includes scatter angle 96 (shown in FIG. 1). Processor 190 relates the energy E to the momentum transfer x by Eq. (1). Mechanical dimensions of secondary collimator 76 (shown in FIG. 1) defines the scatter angle θ. The secondary collimator 76 (shown in FIG. 1) restricts scattered radiation that does not have the angle θ. Processor 190 receives the scatter angle θ from a user, such as a human being, via input device 192.

Processor 190 generates a diffraction profile of substance 82 (shown in FIG. 1) by calculating a number of scatter X-ray photons that are detected by scatter detectors 16 and 18 and by plotting the number of X-ray photons versus the momentum transfer x.

Figure 5:
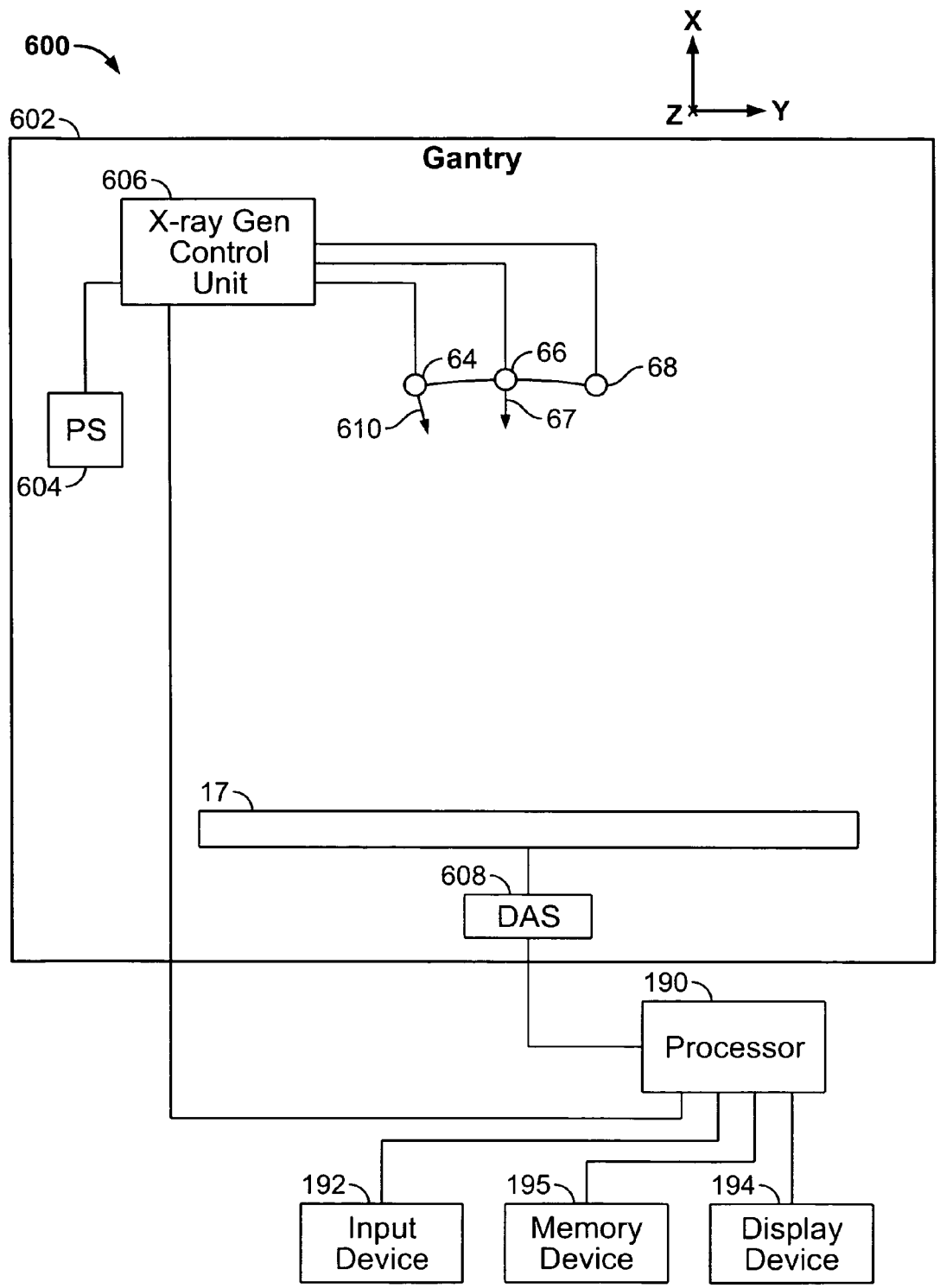

FIG. 5 is a block diagram of an embodiment of a system 600 for reducing a degradation effect on a signal. System 600 includes a gantry 602, processor 190, input device 192, display device 194, and memory device 195. Gantry 602 is an example of gantry 12 (shown in FIG. 1). Gantry 602 includes a power supply 604, an X-ray generation control unit 606, X-ray sources 64, 66, and 68, a data acquisition system (DAS) 608, and transmission detector 17. Alternatively, power supply 604 is located outside gantry 602.

X-ray generation control unit 606 includes a pulse generator (not shown) that is coupled to processor 190 and that receives power from power supply 604. Power supply 604 is coupled to X-ray sources 64, 66, and 68 to supply power to X-ray sources 64, 66, and 68.

Processor 190 issues a command, such as a first on command, a second on command, a first off command, and/or a second off command. Upon receiving the first on command from processor 190, the pulse generator generates a pulse and transmits the pulse to X-ray source 66. Upon receiving a pulse from the pulse generator, X-ray source 66 generates X-ray beam 67 under a potential applied by power supply 604. Similarly, upon receiving the first off command signal from processor 190, the pulse generator stops transmitting a pulse to X-ray source 66 and X-ray source 66 stops generating X-ray beam 67. Furthermore, upon receiving the second on command signal from processor 190, the pulse generator generates and transmits a pulse to any one of the remaining X-ray sources 64 and 68, and any one of the remaining X-ray sources 64 and 68 generates an X-ray beam. For example, upon receiving the second on command signal from processor 190, the pulse generator generates and transmits a pulse to X-ray source 64 and X-ray source 64 generates an X-ray beam 610. In this example, upon receiving the second off command signal from processor 190, the pulse generator stops transmitting a pulse to X-ray source 64, and the X-ray source 64 stops generating an X-ray beam.

DAS 608 receives set 143 of electrical output signals, samples the electrical output signals, and converts the samples to a plurality of digital signals for subsequent processing. Processor 190 receives sampled and digitized data, representing electrical output signals within set 143, such as electrical output signal 196 (shown in FIG. 4), from DAS 608 and performs image reconstruction on the data to generate an X-ray image of substance 82. Moreover, DAS 608 receives set 145 of electrical output signals, samples the electrical output signals, and converts the samples to a plurality of digital signals for subsequent processing. Processor 190 receives sampled and digitized data, representing electrical output signals within set 145, from DAS 608 and performs image reconstruction on the data to generate an X-ray image of substance 82.

Figure 6:
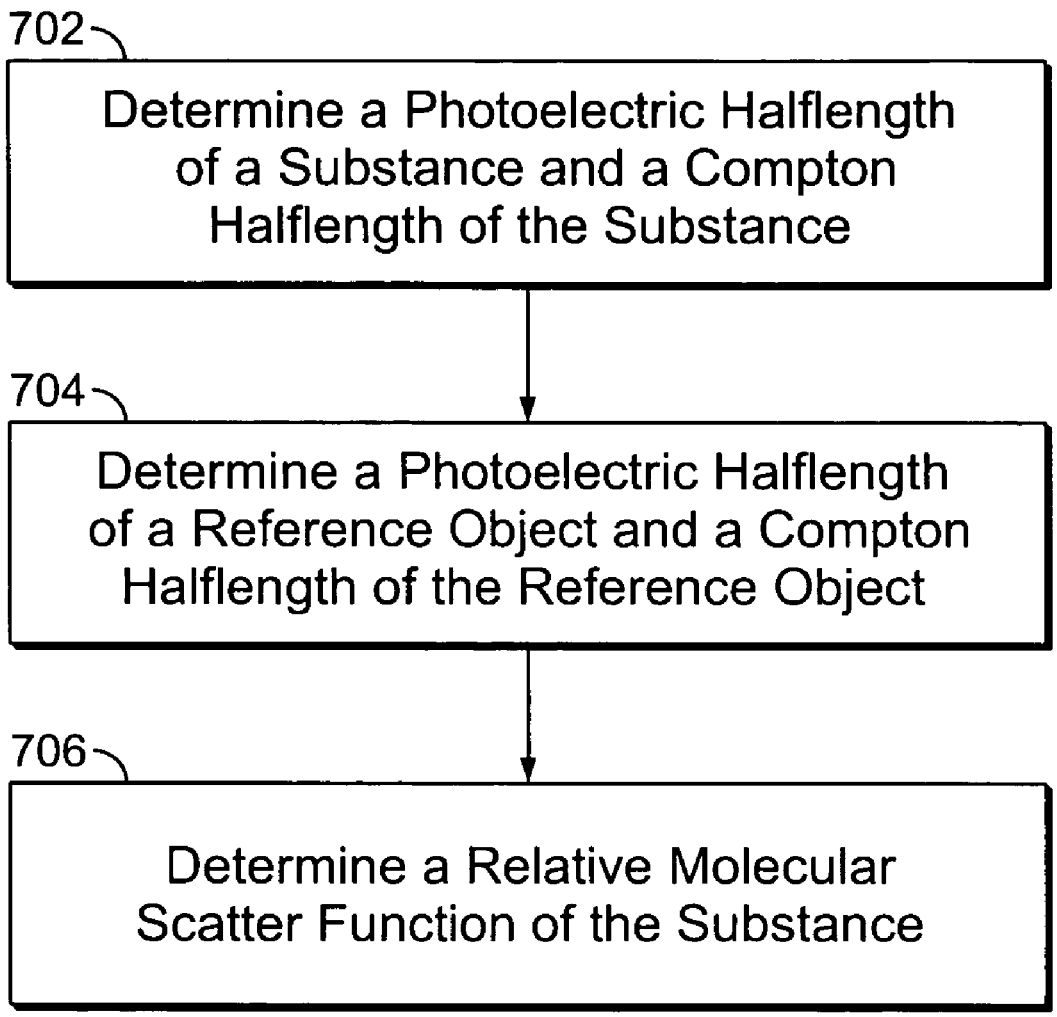

FIG. 6 is a flowchart of an embodiment of a method for reducing a degradation effect on a signal. At block 702, processor 190 determines a Photoelectric pathlength $A_{sub}^P$ of substance 82 and a Compton pathlength $A_{sub}^C$ of substance 82 from sets 143 and 145. An example of determining Photoelectric and Compton pathlengths from electrical signals output by a dual-energy transmission detector is described in a paper, Robert E. Alvarez and Albert Macovski, Energy-selective Reconstructions in X-ray Computerized Tomography, Phys. Med. Biol., 1976, Vol. 21, No. 5, 733-744 (1976).

Processor 190 derives the Photoelectric pathlength $A_{sub}^P$ and the Compton pathlength $A_{sub}^C$ from sampled and digitized data representing dual-energy electrical output signals, such as sets 143 and 145, when a function $f_p(E)$ representing Photoelectric energy dependence and a function $f_C(E)$ representing Compton energy dependence are known. A user provides the functions $f_p(E)$ and $f_C(E)$ via input device 192 to processor 190.

At block 704, processor 190 determines a Photoelectric pathlength $A_{ref}^P$ of reference object 113 and a Compton pathlength $A_{ref}^C$ of reference object 113 from $f_p(E)$, $f_C(E)$, and from sampled and digitized data representing dual-energy electrical output signals output by detector 17 in the same manner as that of determining the Photoelectric pathlength $A_{sub}^P$ and the Compton pathlength $A_{sub}^C$ from $f_p(E)$, $f_C(E)$, and from sampled and digitized data representing sets 143 and 145 except that reference object 113 is scanned within system 10 instead of substance 82 to generate the electrical output signals.

At block 706, processor 190 determines a relative molecular scatter function $\sigma_{sub}^i(E)$ of substance 82 by applying $$\sigma_{sub}^i(E) = \frac{S_{sub}^i(E)\exp\{-(A_{ref}^P f_P(E) + A_{ref}^C f_C(E))\}}{S_{ref}^i(E)\exp\{-(A_{sub}^P f_P(E) + A_{sub}^C f_C(E))\}}, \qquad \text{Eq. (4)}$$

where exp is an exponent, $f_p(E)$ is the Photoelectric energy dependence, $f_C(E)$ is the Compton energy dependence, $S_{sub}^i(E)$ is an intensity of photons detected by an $i^{th}$ detector element, such as one of detector elements 22, 24, 26, 28, 30, 32, 34, and 36 of scatter detector 18 when substance 82 is scanned by system 10, and $S_{ref}^i(E)$ an intensity of photons detected by the $i^{th}$ detector element when reference object 113 is scanned by system 10.

In Eq. (4), processor 190 substitutes $A_{ref}^C$, determined in technique 704, into equation (4). Moreover, in Eq. (4), processor 190 substitutes $A_{ref}^P$, determined in technique 704, into equation (4) Further, in Eq. (4), processor 190 substitutes $A_{sub}^C$, determined in technique 702, into equation (4). Additionally, in Eq. (4), processor 190 substitutes $A_{sub}^P$, determined in technique 702, into equation (4). Moreover, processor 190 substitutes $f_p(E)$ and $f_C(E)$ provided by a user into equation (4). Processor 190 multiplies $f_p(E)$ with $A_{ref}^P$ to generate $A_{ref}^P f_P(E)$ and multiplies $f_P(E)$ with $A_{sub}^P$ to generate $A_{sub}^P f_P(E)$. Processor 190 further multiplies $f_C(E)$ with $A_{sub}^C$ to generate $A_{sub}^C fc(E)$ and multiplies $f_C(E)$ with $A_{ref}^C$ to generate $A_{ref}^C fc(E)$. Processor 190 further calculates a negative of a sum of $A_{ref}^P f_P(E)$ and $A_{ref}^C fc(E)$ and computes a first exponent of the sum. Processor 190 also calculates a negative of a sum of $A_{sub}^P f_P(E)$ and $A_{sub}^C fc(E)$ and computes a second exponent of the sum. Processor 190 multiplies the first exponent by the intensity $S_{sub}^i(E)$ to generate a first term, multiplies the second exponent by the intensity $S_{ref}^i(E)$ to generate a second term, and divides the first term by the second term to generate the relative molecular scatter function $\sigma_{sub}^i(E)$ of substance 82. The techniques illustrated in 702, 704, and 706 are pre-processing that is performed by processor 190. The relative molecular scatter function $\sigma_{sub}^i(E)$ of substance 82 is pre-processed data.

Processor 190 may process the relative molecular scatter function $\sigma_{sub}^i(E)$ to determine a characteristic of substance 82. For example processor 190 computes $\log_e$ of the relative molecular scatter function $\sigma_{relative}^r(E)$ obtained for each $i^{th}$ detector element of scatter detector 18 to generate a relative profile $\log_e(\sigma_{sub}^i(E))$. Processor 190 plots the relative profile as a function of the momentum transfer x based on equation (1) and fits a straight line $m_1 x + c_1$ to the relative profile between a plurality of pre-determined momentum transfer values $x_{sub1}$ and $x_{sub2}$, and calculates an effective atomic number of substance 82 as a function of a gradient $m_1$ of the line $m_1 x + c_1$, where $c_1$ is an intercept of the straight line $m_1 x + c_1$ with either the momentum transfer x of the relative profile or an ordinate of the relative profile. A user provides the pre-determined momentum transfer values $x_{sub1}$ and $x_{sub2}$ to processor 190 via input device 192. As another example, processor 190 determines a straight line $m_2 x + c_2$ from the straight line $m_1 x + c_1$, where $m_2 = -m_1$, $c_2$ is an intercept of the straight line $m_2 x + c_2$ with either an ordinate of the relative profile or the momentum transfer x of the relative profile. Processor 190 determines a difference between the relative profile $\log_e(\sigma_{sub}^i(E))$ and the straight lines $m_1 x + c_1$ and $m_2 x + c_2$. Processor 190 calculates a relative molecular interference function of substance 82 as an antilog of the difference between the relative profile and the straight lines $m_1 x + c_1$ and $m_2 x + c_2$.

Techniques illustrated in FIG. 6 in some instances, may be performed sequentially, in parallel, or in an order other than that which is described. For example, the technique 704 may be performed before performing the technique 702. It should be appreciated that not all of the techniques described are required to be performed, that additional techniques may be added, and that some of the illustrated techniques may be substituted with other techniques.

A technical effect of the herein described systems and methods for reducing a degradation effect on a signal includes using the silver nitrate solution as the white scatterer. Silver has properties that are available in Hubbell, J. H., Veigele, W. J., Briggs, E. A., Brown, R. T., Cromer, D. T., Howerton, R. J., Atomic Form Factors, Incoherent Scattering Functions and Photon Scattering Cross-sections, Journal of Physics and Chemical Reference Data, Volume 4, page 471 (1975), Erratum: Atomic Form Factors, Incoherent Scattering Functions, and Photon Scattering Cross Sections, Journal of Physics and Chemical Reference Data, Volume 6, page 615 (1977). Moreover, when a potential of 24.2 kV is applied to any X-ray source 64, 66, and 68, silver is exposed to primary beams 83 and 84 and a Kα line is emitted. When a potential of 25.6 kV is applied to any X-ray source 64, 66, and 68, silver is exposed to primary beams 83 and 84 and a Kβ line is emitted. In addition, the Kα line and the Kβ line can be used for calibrating scatter detector 18. Other technical effects include placing the silver nitrate solution in the hermetically sealed container, which reduces chances of leakage of the solution. Moreover, chances of decomposition of the silver nitrate solution are lower than that of the conventional reference object. In addition, the silver nitrate solution is easier to manufacture than the conventional reference object.

Yet another technical effect includes performing the pre-processing to reduce an effect of degradation due to self-attenuation of substance 82 on an electrical output signal generated by transmission detector 17. The effect is taken into account by applying Eq. (4) to generate the pre-processed data. The characteristic of substance 82 determined after performing the pre-processing is more accurate than a characteristic determined without performing the pre-processing as a result of the reduction in the effect of degradation.

Another technical effect includes using reference object 113 including an object with an atomic number ranging from and including 40 to 60. The use of the atomic number reduces an effect of scatter by water, which may be mixed with the object within reference object 113.

Exemplary embodiments of systems and methods for reducing a degradation effect on a signal are described above in detail. The systems and methods are not limited to the specific embodiments described herein. For example, the methods may be used in combination with other inspection/detection systems.

While various embodiments of the invention have been described, those skilled in the art will recognize that modifications of these various embodiments of the invention can be practiced within the spirit and scope of the claims.

What is claimed is:

1. A method for reducing a degradation effect on a signal, said method comprising:
    placing a reference object within a housing;
    pre-processing data based on a scan of the reference object and a scan of a substance, wherein the reference object includes a material having an atomic number ranging from and including forty to sixty, wherein data is pre-processed as a function of an intensity of scattered radiation detected by a detector element upon scanning the substance, an intensity of scattered radiation detected by the detector element upon scanning the reference object, a Photoelectric pathlength of the substance, a Compton pathlength of the substance, a Photoelectric pathlength of the reference object, and a Compton pathlength of the reference object.

2. A method in accordance with claim 1, further comprising wherein placing a reference object within a housing comprises confining the reference object within a housing that is opaque to light.

3. A method in accordance with claim 1, further comprising scanning the material comprising silver.

4. A method in accordance with claim 1, further comprising scanning the reference object comprising a silver nitrate solution.

5. A method in accordance with claim 1, further comprising scanning the reference object by using a dual-energy transmission detector.

6. A system for reducing a degradation effect on a signal, said system comprising:
    an X-ray source configured to generate X-rays;
    a reference object configured to output scattered radiation upon receiving the X-rays, the reference object comprising a material having an atomic number ranging from and including forty to sixty;
    a housing configured to contain the reference object;
    a detector configured to output an electrical signal by detecting the scattered radiation; and
    a processor coupled to said detector, said processor configured to generate data as a function of an intensity of the scattered radiation from the reference object and an intensity of scattered radiation from a scanned substance, a Photoelectric pathlength of the substance, a Compton pathlength of the substance, a Photoelectric pathlength of the reference object, and a Compton pathlength of the reference object.

7. A system in accordance with claim 6, wherein the reference object comprises a solution of silver nitrate.

8. A system in accordance with claim 6, wherein the reference object comprises a dilute solution of silver nitrate.

9. A system in accordance with claim 6, wherein the material comprises silver.

10. A system in accordance with claim 6, wherein said housing comprises a plastic material.

11. A system in accordance with claim 6, wherein said housing is configured to hermetically seal the reference object.

12. A system in accordance with claim 6, wherein said housing is opaque to light.

13. A method for reducing a degradation effect on a signal, said method comprising generating pre-processed data as a function of an intensity of scattered radiation detected by a detector element upon scanning a substance, an intensity of scattered radiation detected by the detector element upon scanning a reference object, a Photoelectric pathlength of the substance, a Compton pathlength of the substance, a Photoelectric pathlength of the reference object, and a Compton pathlength of the reference object.

14. A method in accordance with claim 13, further comprising scanning the reference object including a material having an atomic number ranging from and including forty to sixty.

15. A system for reducing a degradation effect on a signal, said system comprising:
    an X-ray source configured to generate X-rays;
    a reference object configured to output a first set of transmission radiation and scattered radiation upon receiving the X-rays;
    a substance configured to output a second set of transmission radiation and scattered radiation upon receiving the X-rays;
    a dual-energy transmission detector configured to detect the transmission radiation within the first and second sets;
    a scatter detector comprising a detector element and configured to detect the scattered radiation within the first and second sets;
    a processor coupled to said dual-energy transmission detector and said scatter detector, wherein said processor is configured to generate pre-processed data as a function of an intensity of the scattered radiation within the first set, an intensity of the scattered radiation within the second set, a Photoelectric pathlength of the substance, a Compton pathlength of the substance, a Photoelectric pathlength of the reference object, and a Compton pathlength of the reference object.

16. A system in accordance with claim 15, wherein the reference object comprises a solution of silver nitrate.

17. A system in accordance with claim 15, wherein the reference object comprises a dilute solution of silver nitrate.

18. A system in accordance with claim 15, wherein the reference object comprises silver.

19. A system in accordance with claim 15, further comprising a reference object housing configured to confine the reference object, wherein the reference object housing is hermetically sealed.

* * * * *